United States Patent [19]

Suzuki et al.

[11] 4,244,873

[45] Jan. 13, 1981

[54] OMEGA-HYDROXY OR ACYLOXY-ALKYL-γ-BUTYROLACTONES

[75] Inventors: Kiyonori Suzuki; Takeaki Eto, both of Noda; Takeyasu Otsuka, Nagareyama; Shozo Abe, Kashiwa; Sadao Yoshikawa, Tokyo, all of Japan

[73] Assignee: Soda Koryo Kabushiki Kaisha, Japan

[21] Appl. No.: 897,641

[22] Filed: Apr. 18, 1978

[30] Foreign Application Priority Data

Apr. 26, 1977 [JP] Japan ............................ 52/47346

[51] Int. Cl.² ........................................... C07D 307/32
[52] U.S. Cl. ........................... 260/343.6; 560/185; 562/579; 260/405; 260/409; 260/410; 260/410.9 R; 260/413
[58] Field of Search ........................................ 260/343.6

[56] References Cited

U.S. PATENT DOCUMENTS

| | | | |
|---|---|---|---|
| 2,364,358 | 12/1944 | Hasche et al. | 260/343.6 |
| 2,892,844 | 6/1959 | Holmquist | 260/343.6 |

FOREIGN PATENT DOCUMENTS 7243546  11/1972  Japan ........................... 260/343.6

OTHER PUBLICATIONS

Nikishin et al., Chem. Abst., 1972, vol. 77, No. 87784v.

*Primary Examiner*—Alan L. Rotman
*Assistant Examiner*—Natalie Harkaway
*Attorney, Agent, or Firm*—Wenderoth, Lind & Ponack

[57] ABSTRACT

Process for preparing omega-hydroxy fatty acids of the formula $$ROCH_2(CH_2)_nCH_2CH_2CH_2COOH$$

wherein

R is H or acyl, and n is an integer of 0 to 18, by a very simple operation without a trouble of pollution, which comprises catalytically reacting an omega-hydroxy (or acyloxy)-alkyl-γ-butyrolactone of the formula

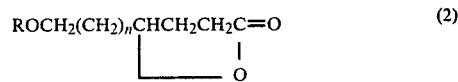 (2)

wherein

R and n are as defined above, in the presence of a hydrogenolysis catalyst.

Compounds of formula (2) are novel, and a process for preparing them is also provided.

14 Claims, No Drawings

OMEGA-HYDROXY OR ACYLOXY-ALKYL-γ-BUTYROLACTONES

This invention relates to a process for preparing omega-hydroxy fatty acids which find extensive use in industry, especially in the oil and fat industry and the perfume industry and are useful as intermediates for organic syntheses, and particularly interesting as intermediates for the production of macrocylic musk perfumes. More specifically, the invention relates to a process for preparing omega-hydroxy fatty acids from inexpensive and readily available materials in high conversions and selectivities by a very simple operation with less process steps. The invention further relates to a process for preparing omega-hydroxy fatty acids which is very advantageous for industrial practice because it can substantially obviate the trouble of waste water treatment.

Numerous methods have been known for the production of omega-hydroxy fatty acids. These methods, however, are industrially disadvantageous because they require many process steps and complicated procedures, involve danger in operation, require expensive reagents, or give poor yields.

For example, a Japanese-language publication "General Treatise on Perfume Chemistry" by Okuda, page 1211, published on Jan. 15, 1968 by Hirokawa Shoten, Tokyo discloses the following process.

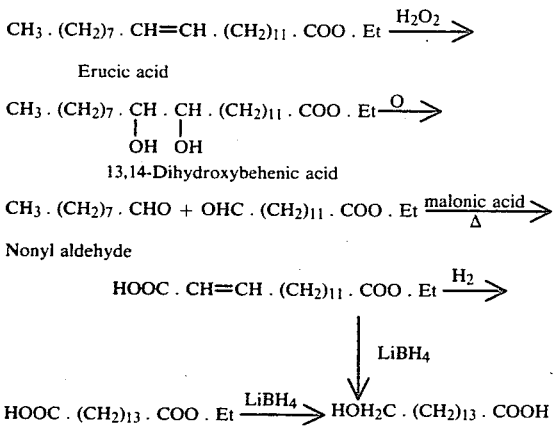

The above known method requires many steps and reactions involving complicated operations and the use of expensive reagents. In addition, the yield obtainable by this method is at most about 40%.

Another method for the synthesis of macrocyclic latones was suggested in 1968 by P. R. Story (J. Am. Chem. Soc. 90, 3, 817). This method involves photochemically decomposing cyclohexanone peroxide in methanol or benzene to yield a macrocyclic lactone together with a macrocyclic hydrocarbon, as schematically shown.

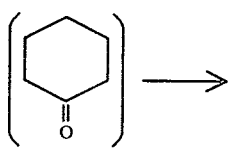

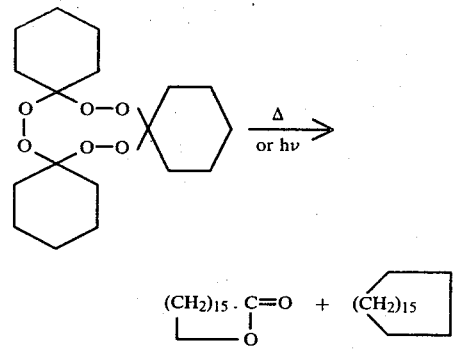

The macrocylic lactone is also formed by heat decomposition of cyclohexanone peroxide. The reaction suggested by Story, however, involves much danger of explosion because of using a peroxide, and is not suited for commercial practice.

The present inventors have made extensive investigations in order to provide a process for preparing omega-hydroxy fatty acids which can overcome the disadvantages of conventional techniques. These investigations led to the discovery that by catalytically reacting an omega-hydroxy (or acyloxy)-alkyl-γ-butyrolactone of the formula

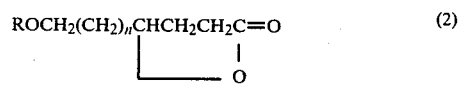

wherein
R represents a hydrogen atom or an acyl group, preferably an acyl group derived from a carboxylic acid having 1 to 10 carbon atoms, and n represents an integer of 0 to 18, in the presence of a hydrogenolysis catalyst, an omega-hydroxy fatty acid of the following formula $$ROCH_2(CH_2)_nCH_2CH_2CH_2COOH \qquad (1)$$

wherein
R and n are as defined above, can be obtained in high conversions and selectivities with commercial advantage.

It has also been found that the butyrolactone of formula (2) can be obtained in high yields by reacting an inexpensive and readily available diol of the formula $$HOCH_2(CH_2)_nCH_2OH \qquad (3)$$

wherein
n is as defined with respect to formula (2),
with acrylic acid or its alkyl ester which is likewise inexpensive and readily available, and has the following formula $$CH_2=CHCOOR' \qquad (4)$$

wherein
R' represents a hydrogen atom or an alkyl group, preferably an alkyl group having 1 to 6 carbon atoms,
in the presence of a radical catalyst, and optionally acylating the resulting omega-hydroxy-alkyl-γ-butyrolactone; and that therefore, omega-hydroxy fatty acids can be prepared from diols and acrylic acid or is alkyl esters in high conversions and selectivities by a very simple operation with two or three steps which are far shorter than in the case of the conventional techniques.

It has further been found that this newly developed process can substantially obviate the trouble of waste water treatment, and is substantially pollution-free and very advantageous industrially.

To the best of the knowledge of the present inventors, the compounds of formula (2) are novel compounds not described in the literature and are useful as perfume compounds. They are useful as intermediates for the production of omega-hydroxy fatty acids and also as intermediates for other organic syntheses.

It is an object of this invention therefore to provide a new process for preparing omega-hydroxy fatty acids with outstanding industrial advantages.

Another object of this invention is to provide novel omega-hydroxy (or acyloxy)-alkyl-$\gamma$-butyrolactones, and a process for preparing these lactones.

The above and other objects and advantages of this invention will become more apparent from the following description.

For easy understanding, the production of the omega-hydroxy fatty acid of formula (1) including the production of the compound of formula (2) from the compounds of formulae (3) and (4) is schematically shown below.

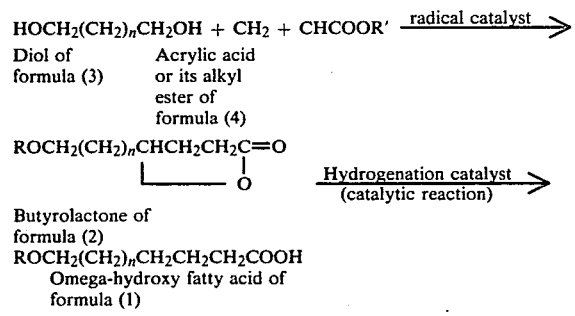

The butyrolactone of formula (2) used in this invention can be obtained easily in high yields by reacting the diol of formula (3) with the acrylic acid or its alkyl ester of formula (4) in the presence of a radical catalyst, and optionally acylating the resulting compound of formula

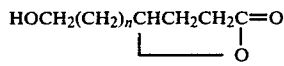

which corresponds to the compound of formula (2) in which R is hydrogen.

Specific examples of the $\alpha,\omega$-diols of formula (3) include ethylene glycol, 1,3-propanediol, 1,4-butanediol, 1,5-pentanediol, 1,6-hexanediol, 1,7-heptanediol, 1,8-octanediol, 1,9-nonanediol, 1,10-decanediol, 1,11-undecanediol, 1,12-dodecanediol, 1,13-tridecanediol, 1,14-tetradecanediol, 1,15-pentadecanediol, 1,16-hexadecanediol, 1,17-heptanediol, and 1,18-octadecanediol. The acrylic acid alkyl ester of formula (4) includes, for example, $C_1$–$C_6$ alkyl esters such as methyl acrylate, ethyl acrylate, n-propyl acrylate, iso-propyl acrylate, n-butyl acrylate, iso-butyl acrylate, sec-butyl acrylate, tert-butyl acrylate, sec-butyl acrylate, tert-butyl acrylate, n-amyl acrylate, iso-amyl acrylate and hexyl acrylate.

Peroxide catalysts are preferred as the radical catalyst used in the reaction, and the use of organic peroxide catalysts is especially preferred. Examples are dialkyl peroxides such as tert-butyl peroxide, hydroperoxides such as tert-butyl hydroperoxide, and diacetyl peroxides such as diacetyl peroxide, and benzoyl peroxide, Di-tertbutyl peroxide (DTBP) is especially advantageous.

The reaction between the diol of formula (3) and the acrylic acid or its alkyl ester of formula (4) can be performed by contacting the compound of formula (3) with the compound of formula (4) in the presence of the radical catalyst. The reaction can be performed in the absence of solvent, but if desired in the presence of an inert liquid solvent. Examples of the liquid solvent are aliphatic ethers such as n-butyl ether, glymes, decalin, and aromatic hydrocarbons such as t-butylbenzene. The reaction is suitably carried out at an elevated temperature under atmospheric pressure to about 20 kg/cm$^2$. The reaction temperature is, for example, about 100° to about 200° C., preferably about 130° to about 170° C., more preferably about 140° to about 160° C. The reaction time can be selected as desired, and can, for example, be about 3 to about 8 hours. The amount of the diol (3) of formula (3) relative to the compound of formula (4) can be properly selected, and is, for example, about 5 to about 15 moles.

When a butyrolactone of formula (2) in which R is an acyl group is used in the process of this invention, the final product can be easily obtained by acylating the omega-hydroxy-alkyl-$\gamma$-butyrolactone obtained as mentioned above. This acylation reaction can be performed easily by reaction with acetic anhydride wherein R is an acetyl group. The reaction can be performed also in the presence of an acid catalyst such as phosphoric acid, sulfuric acid, p-toluenesulfonic acid, or a cation exchange resin such as Amberlist 15 (a tradename for a product of Rohm & Haas Co.). The reaction can be carried out at room temperature to a temperature of about 120° C. for a period of about 1 to about 6 hours. The amount of the acylating agent can be selected as desired. Usually, its amount is from the stoichiometrically required amount to about 5 moles per mole of the compound to be acylated. Examples of the acylating agents include carboxylic acids having 1 to 10 carbon atoms, such as formic acid, acetic acid, propionic acid, butyric acid, isobutyric acid, valeric acid, isovaleric acid, hexylic acid, isohexylic acid, heptylic acid, isoheptylic acid, octylic acid, isooctylic acid, nonylic acid, isononylic acid, benzoic acid, and phenylacetic acid, and anhydrides of these. Of these, n-lower fatty acids and their anhydrides are preferred. The reaction can be performed also in the presence of a solvent, for example aromatic or aliphatic hydrocarbons such as toluene, benzene, hexane or cyclohexane.

The compounds of formula (2) can be obtained by the procedure described above. The resulting compounds of the formula

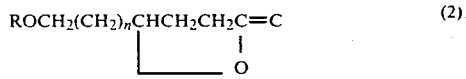

wherein

R represents a hydrogen atom or an acyl group, preferably an acyl group derived from a carboxylic acid having 1 to 10 carbon atoms, and n represents an integer of 0 to 18, preferably 2 to 16, especially preferably 7 to 11, are novel compounds not described in the literature. Specific examples of these omega-hydroxy (or acyloxy)-alkyl-γ-butyrolactones are listed below.

R=H

Omega-hydroxy-methyl (or ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, or nonadecyl)-γ-butyrolactone R=acetoxy omega-acetoxy-alkyl (the same as exemplified above)-γ-butyrolactone R=propoxy omega-propoxy-alkyl (the same as exemplified above)-γ-butyrolactone R=butyloxy omega-butyroxy-alkyl (same as exemplified above)-γ-butyrolactone R=pivaloxy omega-pivaloxy-alkyl (same as exemplified above)-γ-butyrolactone R=isobutyloxy omega-isopivaloxy-alkyl (same as exemplified above)-γ-butyrolactone R=pelargoxy omega-pelargoxy-alkyl (same as exemplified above)-γ-butyrolactone R=benzoyloxy omega-benzoyloxy-alkyl (same as exemplified above)-γ-butyrolactone According to the process of this invention, the omega-hydroxy (or acyloxy)-alkyl-γ-butyrolactone expressed by the following formula

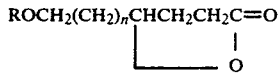
(2)

wherein

R represents a hydrogen atom or an acyl group, and n represents an integer of 0 to 18, is catalytically reacted in the presence of a hydrogenolysis catalyst to afford an omega-hydroxy fatty acid of the formula

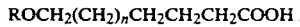
(1)

wherein

R and n are as defined with respect to formula (2), easily in high conversions and selectivities.

An omega-hydroxy-alkyl-γ-butyrolactone of formula (2) in which R is hydrogen can be used in preparing the final omega-hydroxy fatty acid. Preferably, however, compounds of formula (2) in which R is an acyl group are preferred. The reaction can be performed in the copresence of a hydrogen gas in the presence of the hydrogenolysis catalyst. Preferred catalysts are those containing metals of Group VIII of the periodic table, such as palladium and platinum. Preferably, these metal catalysts are used in conjunction with a carrier or promoter such as a solid acid (e.g., cation exchange resins, or zeolites), or a liquid acid (e.g., phosphoric acid, polyphosphoric acid or p-toluenesulfonic acid). If desired, the metal catalyst may be used supported on such a solid acid. Silica gel and silica-alumina gel can also be cited as such a carrier.

Examples of these hydrogenolysis catalysts are noble metal catalysts such as a zeolite-palladium catalyst, a palladium-carbon-cation exchange resin catalyst, a zeolite-platinum catalyst, and a platinum black-cation exchange resin catalyst.

The butyrolactone of formula (2) is reacted catalytically in the presence of the hydrogenation catalyst together with hydrogen gas. The reaction can be carried out in a solvent such as an aliphatic or aromatic alcohol, a fatty acid, an aromatic acid, a hydrocarbon, or a mixture of such a compound with water. Ketones which are converted to the above alcohols by hydrogenation in the reaction system can naturally be used. Alcohols and alcohol-water mixtures, especially an isopropyl alcohol/water mixtures, are preferred.

The reaction can be performed at a temperature of, for example, about 50° to about 250° C., preferably about 100° to about 200° C., more preferably about 130° to 170° C. The reaction pressure may be atmospheric or elevated pressures. Elevated pressures, for example, about 2 to about 150 kg/cm², more preferably about 10 to about 80 kg/cm², are preferred.

The reaction can be performed either batchwise or continuously and either in the liquid phase or in the vapor phase.

The omega-hydroxy fatty acid, for example 15-hydroxy-pentadecanoic acid or 16-hydroxy-hexadecanoic acid, obtained by the process of the present invention can be converted to musk perfuming substances, cyclopentadecanolide and cyclohexadecanolide which are very useful as perfume compounds in good yields.

The following Examples further illustrate the present invention.

EXAMPLE 1 [PREPARATION OF COMPOUND OF FORMULA (2)]

A 1-liter autoclave was charged with 450 g (5 moles) of 1,4-butanediol, and by means of a metering pump, a mixture consisting of 42.5 g (0.5 mole) of methyl acrylate, 42.5 g of decalin and 7.3 g (0.05 mole) of di-t-butyl peroxide (DTBP) was poured into the autoclave at 170° to 180° C. over a period of 5 hours. The gauge pressure at the end of pouring read 15 kg/cm². After the pouring, the mixture was reacted at the same temperature for 1 hour. The reaction mixture was allowed to cool and rectified. Twenty (20) grams of decalin and 390 g of 1,4-butanediol (bp. 140° C./30 mmHg) could be recovered, and 42 g of the reaction product, omega-hydroxy-propyl-γ-butyrolactone (bp. 145° C./1 mmHg), was obtained. The yield of the product was 60% based on the methyl acrylate.

When the above procedure was repeated except that the reaction was carried out at atmospheric pressure at 150° to 170° C., the yield of the final product was 20%.

EXAMPLE 2 [PREPARATION OF COMPOUND OF FORMULA (2)]

1,9-Nonanediol (500 g; 3.13 moles) was placed in a 1-liter three-necked flask, and dissolved and stirred. At 160° to 170° C., a mixture consisting of 26.8 g (0.312 mole) of methyl acrylate, 26.8 g of n-butyl ether and 4.6 g (0.0312 mole) of di-t-butyl peroxide (DTBP) was added dropwise over 5.5 hours. The reaction was continued for 1 hour after the addition, and the reaction mixture was distilled. 450 g of 1,9-nonanediol (bp. 147°-148° C./1 mmHg) was obtained. The desired reaction product, omega-hydroxyoctyl-$\gamma$-butyrolactone, was obtained in an amount of 45 g (bp. 195° C./1 mmHg) in a yield of 68.5% based on methyl acrylate.

EXAMPLE 3 [PREPARATION OF COMPOUND OF FORMULA (2)]

1010 g (5.0 moles) of 1,12-dodecanediol was dissolved, and heated at 160° C. with stirring. A mixture consisting of 43.0 g (0.5 mole) of methyl acrylate, 7.3 g (0.05 mole) of di-t-butyl peroxide (DTBP) and 43.0 g of decalin was added dropwise over a period of 5.5 hours. At the end of the addition, the temperature of the mixture inside the reactor reached 145° C. After the addition, the mixture was reacted at 140° to 160° C. for 1 hour. The reaction mixture was rectified to afford 900 g of 1,12-dodecanediol (bp. 184°-185° C./1 mmHg) and 102.3 g of omega-hydroxyundecyl-$\gamma$-butyrolactone (bp. 217° C./1 mmHg; m.p. 61.5° C.). The yield of the product was 81% based on the methyl acrylate.

EXAMPLE 4 [PREPARATION OF COMPOUND OF FORMULA (2)]

A mixture consisting of 1070 g (5.0 moles) of 1,13-tridecanediol, 43 g of methyl acrylate, 7.3 g of di-tert-butyl peroxide (DTBP) and 43.0 g of decalin was reacted in the same way as in Example 3. Omega-hydroxydodecyl-$\gamma$-butyrolactone (bp. 227° C./1 mmHg) was obtained in a yield of 77% based on the methyl acrylate.

EXAMPLE 5 [PREPARATION OF COMPOUND OF FORMULA (2)]

1150 g (5 moles) of 1,14-tetradecanediol was dissolved, and heated at 160° C. with stirring. A mixture consisting of 43.0 g (0.5 mole) of methyl acrylate, 7.3 g (0.05 mole) of di-t-butyl peroxide and 43 g of decalin was added dropwise over a period of 5.5 hours. After the addition, the mixture was stirred for one hour. The reaction mixture was rectified to separate the 1,14-tetradecanediol and to afford 101.8 g of omega-hydroxytridecyl-$\gamma$-butyrolactone (bp. 230° C./0.8 mmHg) in a yield of 76% based on the methyl acrylate.

EXAMPLE 6 [PREPARATION OF COMPOUND OF FORMULA (2)]

A mixture of 25 g (0.0977 mole) of omega-hydroxyundecyl-$\gamma$-butyrolactone and 40 g (0.39215 mole) of acetic anhydride was reacted with stirring at 115° to 120° C. for 6 hours. After the reaction, the reaction mixture was treated in a customary manner to afford 29.5 g of omega-acetoxyundecyl-$\gamma$-butyrolactone (mp. 36.6° C.) in a yield of 98.5%.

EXAMPLE 7 [PREPARATION OF COMPOUND OF FORMULA (2)]

A mixture of 25 g (0.0977 mole) of omega-hydroxyundecyl-$\gamma$-butyrolactone and 38.1 g (0.293 mole) of acetic anhydride was reacted with stirring at 120° C. for 5 hours. After the addition, the reaction mixture was treated in a customary manner to afford 33.5 g of omega-butyroxyundecyl-$\gamma$-butyrolactone (mp. 24.5° C.) in a yield of 99.0%.

EXAMPLE 8 [PREPARATION OF COMPOUND OF FORMULA (2)]

25 g (0.0977 mole) of omega-hydroxyundecyl-$\gamma$-butyrolactone and 19.9 g (0.1954 mole) of pivalic acid were dissolved in 100 cc of benzene, and were azeotropically dehydrated for 5 hours using two to three drops of conc. sulfuric acid as a catalyst. After the reaction, the unreacted pivalic acid was thoroughly removed with an aqueous solution of sodium carbonate. The residue was washed with water, neutralized, and treated in a customary manner to afford 34.1 g of omega-pivaloxyundecyl-$\gamma$-butyrolactone (mp. 34.7° C.) in a yield of 98.6%.

EXAMPLE 9 [PREPARATION OF COMPOUND OF FORMULA (2)]

The procedure of Example 5 was repeated using a mixture of 26.4 g (0.0977 mole) of omega-hydroxydodecyl-$\gamma$-butyrolactone and 40 g (0.39215 mole) of acetic anhydride. 30.0 g of omega-acetoxydodecyl-$\gamma$-butyrolactone was obtained in a yield of 98%.

EXAMPLE 10 [PREPARATION OF COMPOUND OF FORMULA (2)]

The procedure of Example 7 was repeated using 30.0 g (0.0977 mole) of omega-hydroxydodecyl-$\gamma$-butyrolactone and 20 g (0.195 mole) of n-valeric acid. 35.3 g of omega-valeroxy-dedecyl-$\gamma$-butyrolactone was obtained in a yield of 98.3%.

EXAMPLE 11 [PREPARATION OF COMPOUND OF FORMULA (2)]

25 g (0.0976 mole) of omega-hydroxyundecyl-$\gamma$-butyrolactone and 46.3 g (0.2925 mole) of pelargonic acid were dissolved in 150 cc of benzene, and then azeotropically dehydrated for 6 hours using two to three drops of conc. sulfuric acid as a catalyst. After the reaction, the unreacted palargonic acid was removed with an aqueous solution of sodium carbonate. The residue was washed with water, neutralized, and treated in a customary manner to afford 35.2 g of omega-pelargoxy-undecyl-$\gamma$-butyrolactone (mp. 42.9° C.) in a yield of 91.1%.

EXAMPLE 12 [PREPARATION OF COMPOUND OF FORMULA (2)]

25 g (0.0976 mole) of omega-hydroxyundecyl-$\gamma$-butyrolactone and 47.6 g (0.3904 mole) of benzocic acid were dissolved in 400 cc of toluene, and azeotropically dehydrated for 5 to 6 hours using three to four drops of conc. sulfuric acid as a catalyst. After the reaction, the reaction mixture was thoroughly washed with sodium carbonate, and then treated in a customary manner to afford 29.5 g of omega-benzoyloxyundecyl-$\gamma$-butyrolactone (mp. 82.0° C.) in a yield of 84.0%.

EXAMPLE 13 [PREPARATION OF A HYDROGENATION CATALYST]

50 g of NaY-type zeolite, 14.42 g of ammonium nitrate and 1800 g of deionized water were placed in a 2-liter three-necked flask, and stirred for 30 minutes at 70° to 80° C. to perform ion exchange. After the end of ion exchange, the mixture was filtered, and the precipitate was washed with 2000 g of ion exchange water. The ion exchange washing procedure was repeated two times more. In the final washing, 3000 g of deionized water was used. After the washing, the product was dried at room temperature and then at 125° C. for 5 hours. Thus, 45 g of ion-exchanged zeolite was obtained. A flask was charged with 45 g of this zeolite and 225.0 g of deionized water, and a solution obtained by dissolving 0.753 g of palladium chloride in 6 ml of 28% ammonia solution and diluting the solution with 45 ml of deionized water was poured at 30° C. The mixture was stirred at the same temperature for 1 hour to deposit the palladium chloride on the zeolite. The precipitate was filtered, washed fully with deionized water, dried at 120° C. for 5 hours, and calcined at 350° to 400° C. for 9 hours. The product was then activated for 10 hours in a hydrogen stream at 450° to 500° C. to obtain 40 g of a PdHY-type zeolite catalyst [which is designated as PdHY-type zeolite catalyst (I)].

EXAMPLE 14 [PREPARATION OF A HYDROGENATION CATALYST]

The product obtained by calcining at 350° to 400° C. for 9 hours in the procedure of Example 10 without further activation can be used as a catalyst. This catalyst is designated as PdHY-type zeolite catalyst (II).

EXAMPLE 15 [PREPARATION OF A HYDROGENATION CATALYST]

40 g of ion-exchanged zeolite obtained by the same method as in Example 10, and 200 ml of deionized water were charged into a flask, and a solution of 1.2 g of $Pt(NH_3)_4Cl_2H_2O$ in 260 g of deionized water was added dropwise with stirring over the course of 10 to 12 hours to deposit the platinum compound on the zeolite. The resulting slurry was filtered, washed with deionized water, dried at 125° C., and calcined at 350° to 400° C. The calcined product was activated in a stream of hydrogen at 450° to 500° C. for 10 hours to afford a PtHY-type zeolite catalyst.

EXAMPLE 16 [PREPARATION OF COMPOUND OF FORMULA (1)]

An autoclave was charged with 20 g (0.078 mole) of omega-hydroxyundecyl-γ-butyrolactone, 1.0 g of the PdHY-type zeolite catalyst (I) and 1.5 g of 80% isopropanol (containing 20% of water), and the butyrolactone was hydrogenolyzed at 158° to 160° C. for 3 hours while maintaining the initial pressure of hydrogen at 66.1 kg/cm². After the reaction, the catalyst was removed by filtration, and 20 g of an oily reaction product was obtained.

Quantitative determination of the oily reaction product by G.L.C. showed that 1.1 g (0.0045 mole) of pentadecanoic acid, 4.5 g (0.0187 mole) of γ-pentadecalactone, 10.9 g (0.0422 mole) of 15-hydroxypentadecanoic acid, and 2.9 g (0.0011 mole) of the unreacted omega-hydroxyundecyl-γ-butyrolactone were obtained.

$$\text{Conversion } (\frac{0.0045 + 0.0187 + 0.0422}{0.0781} \times 100) = 83.7\%$$

$$\text{Selectivity } (\frac{0.0422}{0.0781 - 0.011} \times 100) = 62.9\%$$

Hence, the yield of 15-hydroxypentadecanoic acid was 62.9% based on the omega-hydroxyundecyl-γ-butyrolactone.

EXAMPLE 17 [PREPARATION OF COMPOUND OF FORMULA (1)]

The same reaction as in Example 16 was carried out using 20 g (0.0781 mole) of omega-hydroxyundecyl-γ-butyrolactone, 1.2 g of the PtHY-type zeolite catalyst, and 1.5 g of 80% isopropanol (containing 20% of water). The conversion to 15-hydroxypentadecanoic acid was 80.7%, and its selectivity was 60.3%.

EXAMPLE 18 [PREPARATION OF COMPOUND OF FORMULA (1)]

An autoclave was charged with 29.5 g (0.0962 mole) of omega-acetoxyundecyl-γ-butyrolactone, 1.24 g of the PdHY-type zeolite catalyst (I) and 1.9 g of 80% isopropanol (containing 20% of water), and the butyrolactone was hydrogenolyzed at 144° to 156° C. for 3.5 hours while maintaining the initial pressure of hydrogen at 60 kg/cm². After the reaction, the catalyst was separated by filtration. The residue was treated in a customary manner to afford 28.6 g of the final product which consisted of 0.3 g (0.0011 mole) of pentadecanoic acid, 1.7 g (0.007 mole) of γ-undecylbutyrolactone, 25.2 g (0.0841 mole) of 15-acetoxypentadecanoic acid and 1.2 g (0.0039 mole) of the unreacted omega-acetoxyundecyl-γ-butyrolactone.

$$\text{Conversion } (\frac{0.0011 + 0.007 + 0.0841}{0.09622} \times 100) = 95.8\%$$

$$\text{Selectivity } (\frac{0.0841}{0.09622 - 0.00395} \times 100) = 91.1\%$$

Hence, the yield of 15-acetoxypentadecanoic acid was 91.1% based on the consumed omega-acetoxyundecyl-γ-butyrolactone.

EXAMPLE 19 [PREPARATION OF COMPOUND OF FORMULA (1)]

The same reaction as in Example 18 was performed using 29.5 g (0.0962 mole) of omega-acetoxyundecyl-γ-butyrolactone, 1.3 g of the PdHY-type zeolite catalyst (II), and 1.9 g of 80% isopropanol (containing 20% of water). The conversion to 15-acetoxypentadecanoic acid was 93.0%, and the selectivity was 87.0%.

EXAMPLE 20 [PREPARATION OF COMPOUND OF FORMULA (1)]

The same reaction as in Example 18 was carried out using 30.0 g (0.0978 mole) of omega-acetoxyundecyl-γ-butyrolactone, 1.2 g of the PtHY-type zeolite catalyst, and 2.0 g of 80% isopropanol (containing 20% of water). The conversion to 15-acetoxypentadecanoic acid was 96%, and the selectivity was 89.2%.

EXAMPLE 21 [PREPARATION OF COMPOUND OF FORMULA (1)]

The same reaction as in Example 18 was performed using 29.0 g (0.089 mole) of omega-butyroxyundecyl-γ-butyrolactone, 1.0 g of the PdHY-type zeolite catalyst (I), and 2.0 g of 80% isopropanol (containing 20% of water). Analysis of the product showed that the conversion was 72%, and the selectivity was 75%.

EXAMPLE 22 [PREPARATION OF COMPOUND OF FORMULA (1)]

The same reaction as in Example 18 was carried out using 30.0 g (0.088 mole) of omega-pivaloxyundecyl-γ-butyrolactone, 1.0 g of the PdHY-type zeolite catalyst (I), and 2.0 g of 80% isopropanol (containing 20% of water). Analysis of the product showed that the conversion was 70% and the selectivity was 80%.

EXAMPLE 23 [PREPARATION OF COMPOUND OF FORMULA (1)]

The same reaction as in Example 18 was carried out using 31 g (0.075 mole) of omega-pelargoxyundecyl-γ-butyrolactone, 1.1 g of the PdHY-type zeolite catalyst (I), and 2.0 g of 80% isopropanol (containing 20% of water). Analysis of the product showed that the conversion was 72%, and the selectivity was 70.0%.

EXAMPLE 24 [PREPARATION OF COMPOUND OF FORMULA (1)]

The same reaction as in Example 18 was carried out using 27.0 g (0.0730 mole) of omega-benzoyloxyundecyl-γ-butyrolactone, 1.0 g of the PdHY-type zeolite catalyst (I), and 2.0 g of 80% isopropanol (containing 20% of water). Analysis of the product showed that the conversion was 85%, and the selectivity was 43%.

EXAMPLE 25 [PREPARATION OF COMPOUND OF FORMULA (1)]

The same reaction as in Example 18 was carried out using 29.0 g (0.089 mole) of omega-butyroxyundecyl-γ-butyrolactone, 1.0 g of the PtHY-type zeolite catalyst, and 2.0 g of 80% isopropanol (containing 20% of water). Analysis of the product showed that the conversion to the desired omega-butyroxy-pentadecanoic acid was 80%, and the selectivity was 70%.

EXAMPLE 26 [PREPARATION OF COMPOUND OF FORMULA (1)]

The same reaction as in Example 18 was carried out using 30.0 g (0.088 mole) of omega-pivaloxyundecyl-γ-butyrolactone, 1.0 g of the PtHY-type zeolite catalyst and 2.0 g of 80% isopropanol (containing 20% of water). The conversion to the final product was 82%, and the selectivity was 78%.

EXAMPLE 27 [PREPARATION OF COMPOUND OF FORMULA (1)]

An autoclave was charged with 23.9 g (0.0788 mole) of omega-acetoxyundecyl-γ-butyrolactone, 1.0 g of 5% Pd-C, 1.5 g of a cation exchange resin (Amberlist 15), and 1.5 g of 80% isopropanol (containing 20% of water), and the butyrolactone was hydrogenolyzed at 134° to 144° C. for 5 hours while maintaining the initial pressure of hydrogen at 63.5 kg/cm². After the reaction, the catalyst was removed by filtration, and the residue was treated in a customary manner to afford 24 g of the desired product which consisted of 0.4 g (0.0016 mole) of pentadecanoic acid, 0.9 g (0.0036 mole) of γ-pentadecalactone, 18.8 g (0.0626 mole) of 15-acetoxypentadecanoic acid and 3.0 g (0.0099 mole) of the unreacted omega-acetoxyundecyl-γ-butyrolactone.

Conversion ( $\frac{0.0016 + 0.0036 + 0.0626}{0.0788}$ × 100) = 86.0%

Selectivity ( $\frac{0.0626}{0.0788 - 0.0099}$ × 100) = 90.9%

Hence, the yield of 15-acetoxypentadecanoic acid based on the consumed omega-acetoxyundecyl-γ-butyrolactone was 92.3%.

EXAMPLE 28 [PREPARATION OF COMPOUND OF FORMULA (1)]

An autoclave was charged with 30.2 g (0.0953 mole) of omega-acetoxydodecyl-γ-butyrolactone, 1.3 g of the PdHY-type zeolite catalyst (I), and 1.9 g of 80% isopropanol (containing 20% of water), and the butyrolactone was hydrogenolyzed at 144° to 157° C. for 3.5 hours while maintaining the initial pressure of hydrogen at 65 kg/cm².

After the reaction, the catalyst was separated by filtration, and the residue was treated in a customary manner to afford 30 g of a product which consisted of 0.8 g (0.003 mole) of hexadecanoic acid, 1.8 g (0.0071 mole) of γ-hexadecalactone 24.5 g (0.0779 mole) of 16-acetoxyhexadecanoic acid, and 2.3 g (0.0073 mole) of the unreacted omega-acetoxydodecyl-γ-butyrolactone.

Conversion ( $\frac{0.003 + 0.0071 + 0.0779}{0.0953}$ × 100) = 92.3%

Selectivity ( $\frac{0.0779}{0.0953 - 0.0073}$ × 100) = 88.5%

Hence, the yield of 16-acetoxyhexadecanoic acid based on the consumed omega-acetoxydodecyl-γ-butyrolactone was 88.5%.

What we claim is:

1. An omega-hydroxy or omega-acyloxy-alkyl-γ-butyrolactone of the formula

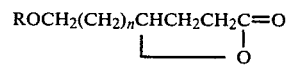

wherein R represents a hydrogen atom or an acyl group derived from an acyclic monocarboxylic acid having 1 to 10 carbon atoms, benzoic acid or phenylacetic acid and n represents an integer of 7 to 11.

2. An omega-hydroxy-alkyl-γ-butyrolactone of the formula

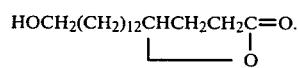

3. An omega-hydroxy-alkyl-γ-butyrolactone of claim 1.

4. An omega-acyloxy-alkyl-γ-butyrolactone of claim 1.

5. The compound according to claim 3 wherein n=7 and R=hydrogen.

6. The compound according to claim 3 wherein n=10 and R=hydrogen.

7. The compound according to claim 3 wherein n=11 and R=hydrogen.

8. The compound according to claim 4 wherein R=acetyl and n=10.

9. The compound according to claim 4 wherein R=butyryl and n=10.

10. The compound according to claim 4 wherein R=pivaloyl and n=10.

11. The compound according to claim 4 wherein R=acetyl and n=11.

12. The compound according to claim 4 wherein R=pelargonyl and n=11.

13. The compound according to claim 4 wherein R=valeryl and n=10.

14. The compound according to claim 4 wherein R=benzoyl and n=10.

* * * * *